(12) United States Patent
Hazen et al.

(10) Patent No.: US 7,459,286 B1
(45) Date of Patent: *Dec. 2, 2008

(54) ASSESSING THE RISK OF A MAJOR ADVERSE CARDIAC EVENT IN PATIENTS WITH CHEST PAIN

(75) Inventors: Stanley L. Hazen, Pepper Pike, OH (US); Marc S. Penn, Beachwood, OH (US); Renliang Zhang, Beachwood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 245 days.

This patent is subject to a terminal disclaimer.

(21) Appl. No.: 10/972,058

(22) Filed: Oct. 22, 2004

Related U.S. Application Data

(60) Provisional application No. 60/513,490, filed on Oct. 22, 2003.

(51) Int. Cl.
    *C12Q 1/28*     (2006.01)
    *G01N 33/48*     (2006.01)

(52) U.S. Cl. .......................... 435/28; 426/63

(58) Field of Classification Search ............ None
See application file for complete search history.

(56) References Cited

U.S. PATENT DOCUMENTS

| | | | |
|---|---|---|---|
| 5,122,534 A | 6/1992 | Loose et al. | |
| 5,731,208 A | 3/1998 | Heinecke | |
| 5,747,274 A | 5/1998 | Jackowski | |
| 5,871,946 A | 2/1999 | Lucas et al. | |
| 5,889,042 A | 3/1999 | MacLean et al. | |
| 5,985,272 A | 11/1999 | Deby et al. | |
| 6,096,556 A | 8/2000 | Heinecke | |
| 6,133,039 A | 10/2000 | Heinecke | |
| 6,268,220 B1 | 7/2001 | Heinecke | |
| 6,953,666 B1 | 10/2005 | Kinkade, Jr. et al. | |
| 7,223,552 B2 * | 5/2007 | Hazen et al. ............ | 435/7.24 |
| 2002/0164662 A1 | 11/2002 | Hazen et al. | |
| 2003/0119792 A1 | 6/2003 | Roca | |
| 2003/0180218 A1 | 9/2003 | Hazen | |
| 2006/0051872 A1 | 3/2006 | Sailor et al. | |

FOREIGN PATENT DOCUMENTS

| | | |
|---|---|---|
| EP | 0 389 381 | 9/1990 |
| EP | 0 418 486 | 3/1991 |
| WO | 96/04311 | 2/1996 |
| WO | 02/48715 | 6/2002 |
| WO | 02/50550 | 6/2002 |
| WO | WO 02/062207 | 8/2002 |

OTHER PUBLICATIONS

Baldus S et al (published online Sep. 2, 2003) Myeloperoxidase serum levels predict risk in patients with acute coronary syndromes. Circulation, vol. 108, pp. 1440-1445.*

Biasucci LM et al (1996) Intracellular neutrophil myeloperoxidase is reduced in unstable angina and acute myocardial infarction, but its reduction is not related to ischemia. J Amer Coll Cardiol, vol. 27, No. 3, pp. 611-616.*

Zhang R et al (Mar. 1, 2002) Defects in leukocyte-mediated initiation of lipid peroxidation in plasma as studied in myeloperoxidase-deficient subjects: systematic identification of multiple endogenous diffusable substrates for myeloperoxidase in plasma. Blood, vol. 99, No. 5, pp. 1802-1810.*

"Association Between Myeloperoxidase Levels and Risk of Coronary Artery Disease" by Zhang, et al., *JAMA*, vol. 286, No. 17, Nov. 7, 2001, pp. 2136-2142.

"Is the Oxidative Modification Hypothesis Relevant to Human Atherosclerosis? Do the Antioxidant Trials Conducted to Date Refute the Hypothesis?" by Steinberg, et al., *Circulation*, 2002; 105:2107-2111.

"Myeloperoxidase Deficiency" by Nauseef, *Hematology, Oncology Clinics of North America*, vol. 2, No. 1, Mar. 1988, pp. 135-158.

"Primary Inherited Defects in Neutrophil Function: Etiology and Treatment" by Malech, et al., *Seminars in Hematology*, vol. 34, No. 4, Oct. 1997, pp. 279-290.

"Mass spectrometric quantification of amino acid oxidation products in proteins: insights into pathways that promote LDL oxidation in the human artery wall" by Heinecke, et al., *FASEB J.*, 13, 1113-1120 (1999).

"Myeloperoxidase-Generated Oxidants and Atherosclerosis" by Podrez, et al., *Free Radical Biology & Medicine*, vol. 28, No. 12, pp. 1717-1725, Jan. 2000.

"Myeloperoxidase, a Catalyst for Lipoprotein Oxidation, Is Expressed in Human Atherosclerosis Lesions" by Daugherty, et al., *J. Clin. Invest.*, vol. 94, Jul. 1994, 437-444.

(Continued)

*Primary Examiner*—Jon P Weber
*Assistant Examiner*—Paul C. Martin
(74) *Attorney, Agent, or Firm*—Calfee, Halter & Griswold LLP

(57) ABSTRACT

Methods for characterizing the near term risk of experiencing a major adverse cardiac event in a patient presenting with chest pain are provided. In one embodiment the method comprises determining the level of myeloperoxidase (MPO) activity in a bodily sample obtained from the patient. In another embodiment, the method comprises determining the level of MPO mass in a bodily sample obtained from the patient. In another embodiment, the method comprises determining the level of one or more select MPO-generated oxidation products in a bodily sample obtained from the patient. The select MPO-generated oxidation products are dityrosine, nitrotyrosine, chlorotyrosine, methionine sulphoxide or an MPO-generated lipid peroxidation product. Levels of MPO activity, MPO mass, or the select MPO-generated oxidation product in bodily samples from the test subject are then compared to a control value that is derived from measurements of MPO activity, MPO mass, or the select MPO-generated oxidation product in comparable bodily samples obtained from control population. Such comparison can also be used to determine treatment of the patient immediately at presentation in the emergency room.

24 Claims, 2 Drawing Sheets

OTHER PUBLICATIONS

"3-Chlorotyrosine, a Specific Marker of Myeloperoxidase-catalyzed Oxidation, Is Markedly Elevated in Low-Density Lipoprotein Isolated from Human Atherosclerosis Intima" by Hazen, et al., *J. Clin. Invest.*, vol. 99, No. 9, May 1997, 2075-2081.

Elevated levels of protein-bound *p*-hydroxyphenylacetaldehyde, an amino acid-derived aldehyde generated by myeloperoxidase, are present in hun fatty streaks, intermediate lesions and advanced atherosclerosis lesions by Hazen, et al., *Biochem J.* (2000) 352, 693-699.

"*p*-Hydroxypheylacetaldehyde, an Aldehyde Generated by Myeloperoxidase, Modifies Phospholipid Amino Groups of Low Density Lipoprotein in Human Atherosclerosis Intima" by Heller, et al., *The Journal of Biological Chemistry*, vol. 275, No. 14, Apr. 7, 2000, pp. 9957-9962.

International Search Report dated Jul. 31, 2002.

"Oxidized LDL and HDL: antagonists in atherothrombosis" by Mertens, et al., *FASEB J.*, 15, 2073-2084 (2001).

"Macrophage scavenger receptor CD36 is the major receptor for LDL modified by monocyte-generated reactive nitrogen species" by Podrez, et al., *J. Clin. Invest.* 105:1095-1108 (2000).

"Inhibition of Adhesion Molecules Markedly Ameliorates Cytokine-Induced Sustained Myocardial Dysfunction in Dogs in vivo" by Momii, et al., *J. Mol. Cell. Cardiol.* 30, 2637-2650 (1998).

"Supplemention with Tetrahydrobiopterin Suppresses the Development of Hypertension in Spontaneously Hypertension Rats" by Hong, et al., *Hypertension*, 2001; 38:1044-1048.

Supplementary European Search Report dated Jan. 29, 2004.

"Kinetics of Oxidation of Tyrosine and Dityrosine by Myeloperoxidase Compounds I and II" by Marquez, et al., *The Journal of Biological Chemistry*, vol. 270, No. 51, Dec. 22, 1995, pp. 30434-30440.

"Leukocytes Utilize Myeloperoxidase-Generated Nitrating Intermediates as Physiological Catalysts for the Generation of Biologically Active Oxidized Lipids and Sterols in Serum" by Schmitt, et al., *Biochemistry*, 1999, 38, 16904-16915.

"Nitric Oxide Modulates the Catalytic Activity of Myeloperoxidase" by Abu-Soud, et al., *The Journal of Biological Chemistry*, vol. 275, No. 8, Feb. 25, 2000, pp. 5425-5430.

"Circulating Myeloperoxidase and Anti-Myeloperoxidase Antibody in Patients with Vasculitis" by Minota, et al., *Scand J. Rheumatol*, 1999;25:94-9.

"Primary Prevention of Acute Coronary Events with Lovastatin in Men and Women with Average Cholesterol Levels" by Downs, et al., *JAMA*, May 27, 1998, vol. 279, No. 20, pp. 1615-1622.

"The Effect of Pravastatin on Coronary Events After Myocardial Infarction in Patients with Average Cholesterol Levels" by Sacks, et al., *The New England Journal of Medicine*, vol. 335, No. 14, Oct. 3, 1996, pp. 1001-1009.

"Byeond Cholesterol: Modifications of Low-Density Lipoprotein that Increase its Atherogenecity" by Steinberg, et al., *The New England Journal of Medicine*, vol. 320, No. 14, Apr. 16, 1989, pp. 915-924.

"Pleiotropic Effects of 3-Hydroxy-3-Methylglutaryl Coenzyme A Reductase Inhibitors" by Takemoto, et al., *Arterioscler Throm Vasc Biol*, 2001;21:1712-1719.

"The Evolving Role of Statins in the Management of Atherosclerosis" by Vaughan, et al., *Journal of the American College of Cardiology*, vol. 35, No. 1, 2000, pp. 1-10.

"Reduction of Plasma 24S-Hydroxycholesterol (Cerebrosterol) Levels Using High-Dosage Simvastatin in Patients with Hypercholesterolemia" by Locatelli, et al., *Arch Neurol*, vol. 59, Feb. 2002, pp. 213-216.

"Alzehimer's Disease: Bad for the Heart, Bad for the Mind" by Marx, *Science*, vol. 294, Oct. 19, 2001, pp. 508-509.

3-Hydroxy-3-methylglutaryl-coenzyme A reductase in mRNA in Alzheimer and control brain by Yasojima, et al., *Clinical Neuroscience and Neuropathology*, vol. 12, No. 13, Sep. 17, 2001, pp. 2935-2938.

"Lovastatin Treatment Decreases Mononuclear Cell Infiltration Into the CNS of Lewis Rats with Experimental Allergic Encephalomyelitis" by Stanislaus, et al., *Journal of Neuroscience Research*, 66:155-162 (2001).

"Effect of Hydroxymethylglutaryl Coenzyme A Reductase Inhibitors on the Progression of Calcific Aortic Stenosis" by Novaro, et al., *Circulation*, 2001; 104-2205-2209.

"Measurement of C-Reactive Protein for the Targeting of Statin Therapy in the Primary Prevention of Acute Coronary Events" by Ridker, et al., *The New England Journal of Medicine*, vol. 344, No. 26, Jun. 28, 2001, pp. 1959-1965.

"Rapid Reduction in C-Reactive Protein with Cerivastatin Among 785 Patients with Primary Hypercholesterolemia" by Ridker, *Circulation*, 2001; 103:1191-1193.

"Are Statins Anti-Inflammatory? Issues in the Design and Conduct of the Pravastatin Inflammation C-Reactive Proetin Evaluation" by Ridker, et al., *Current Cardiology Reports*, 2000, 2:269-273.

Supplementary Partial European Search Report dated May 31, 2007.

"Association of Nitrotyrosine Levels With Cardiovascular Disease and Modulation by Statin Therapy" by Shishehbor, et al., JAMA, Apr. 2, 2003, vol. 289, No. 13, pp. 1675-1680.

"Associations between change in C-reactive protein and serum lipids during statin treatment" by Standberg, et al., The Finnish Medical Society Duodecim, Ann Med 2000; 32:579-583.

"Effects of Low Doses of Simvastatin and Atorvastatin on High-Density Lipoprotein Cholesterol Levels in Patients with Hypercholesterolemia" by Branchi, et al., Clinical Therapeutics, vol. 23, No. 6, 2001, pp. 851-857.

"Modification of Proteins and Lipids by Myeloperoxidase" by Hazen, et al., Methods in Enzymology, vol. 300, 1999, pp. 88-105.

"Mechanisms of oxidative damage by myeloperoxidase in atherosclerosis and other inflammatory disorders" by Heinecke, et al., J Lab Clin Med 1999; 133:321-5.

"The oxidative modification hypothesis of atherogenesis: an overview" by Chisolm, et al., Free Radical Biology & Medicine, vol. 28, No. 12, pp. 1815-1826, 2000.

"Myeloperoxidase binds to low-density lipoprotein: potential implications for atherosclerosis" by Carr, et al., FEBS Letters 487 (2000) 176-180.

"Comparison of Troponin T Versus Creatine Kinase-MB in Suspected Acute Coronary Syndromes" by McErlean, et al., Am J Cardiol 2000;85:421-426.

"Multimarker Approach to Risk Stratification in Non-ST Elevation Acute Coronary Syndromes: Simultaneous Assessment of Troponin I, C-Reactive Protein, and B-Type Natriuretic Peptide" by Sabatine, et al., Circulation 2002;105:1760-1763.

"Cardiac-Specific Troponin I Levels to Predict the Risk of Martality in Patients with Acute Coronary Syndromes" by Antman, N. Engl J Med 1996;335:1342-9.

"Ability of Troponins to Predict Adverse Outcomes in Patients with Renal Insufficiency and Suspected Acute Coronary Syndromes: A Case-Matched Study" by Van Lente, et al., J Am Coll Cardiol 1999;33:471-8.

Abstract—"Elevated Levels of Plasma Myeloperoxidase, an Oxidative Enzyme Degranulated from Activated Phagocytes, in Patients with Coronary Artery Disease and Acute Coronary Syndromes" by Sugiyama, et al., Supplement to Circulation, vol. 106, No. 19, Nov. 5, 2002, Abstracts from Scientific Sessions, McCormick Place, Chicago, Illinois, Nov. 17-20, 2002.

"Extensive Nitration of Protein Tyrosines in Human Atherosclerosis Detected by Immunohistochemistry" by Beckmann, et al., Biol. Chem. Hoppe-Seyler, vol. 375, pp. 81-88, Feb. 1994.

"Widespread Coronary Inflammation in Unstable Angina" by Buffon, et la., N Engl J Med 2002; 347:5-12.

"Thrombosis and Acute Coronary-Artery Lesions in Sudden Cardiac Ischemic Death" by Davies, et al., N. Engl. J Med 1984; 310:1137-40.

"Increased Neutrophil Elastase Release in Unstable Angina Pectoris and Acute Myocardial Infarction" by Dinerman, et al., J Am Coll Cardiol 1990; 15:1559-63.

"Do Human Atherosclerotic Lesions Contain Nitrotyrosine?" by Evans, et al., Biochemical and Biophysical Research Communications 226, 346-351 (1996).

"Extensive tryosine nitration in human myocardial inflammation: evidence for the presence os peroxynitrite" by Kooy, et al. Crit Care Med, vol. 25(5) May 1997, 812-819.

"Reactive Nitrogen Intermediates Promote Low Density Lipoprotein Oxidation in Human Atherosclerotic Intima" by Leeuwenburgh, et al., The Journal of Biological Chemistry, vol. 272, No. 3, Jan. 17, 1997, 1433-1436.

"Nitrotyrosine Bound to beta-VLDL-Apoproteins: A Biomarker of Peroxynitrite Formation in Experimental Atherosclerosis" by Moriel, et al., Biochemical and Biophysical Research Communications 232, 332-335 (1997).

"Neutrophil Infiltration of Culprit Lesions in Acute Coronary Syndromes" by Naruko, et al., Circulation, 2002; 106:2894-2900.

"Myeloperoxidase-generated reactive nitrogen species convert LDL into an atherogenic form in vitro" by Podrez, et al., J. Clin. Invest. 103:1547-1560 (1990).

"How urine analysis reflects oxidative stress—nitrotyrosine as a potential marker" by Schwemmer, et al., Clinica Chimica Acta 297 (2000) 207-216.

Non-Final Office Action dated Oct. 4, 2004, for U.S. Appl. No. 10/039,753, filed Jan. 2, 2002.

Non-Final Office Action dated Mar. 24, 2005, for U.S. Appl. No. 10/039,753, filed Jan. 2, 2002.

Non-Final Office Action dated Mar. 10, 2006, for U.S. Appl. No. 10/039,753, filed Jan. 2, 2002.

Final Office Action dated Jul. 3, 2006, for U.S. Appl. No. 10/039,753, filed Jan. 2, 2002.

Non-Final Office Action dated Aug. 17, 2006, for U.S. Appl. No. 10/039,753, filed Jan. 2, 2002.

Final Office Action dated Nov. 22, 2006, for U.S. Appl. No. 10/039,753, filed Jan. 2, 2002.

Advisory Action dated Dec. 28, 2006, for U.S. Appl. No. 10/039,753, filed Jan. 2, 2002.

Advisory Action dated Feb. 21, 2007, for U.S. Appl. No. 10/039,753, filed Jan. 2, 2002.

U.S. Appl. No. 10/417,838, filed Apr. 17, 2003, entitled: "Systemic Marker for Monitoring Anti-Inflammatory and Antioxidant Actions of Therapeutic Agents".

"Myeloperoxidase Functions as a Major Enzymatic Catalyst for Initiation of Lipid Peroxidation at Sites of Inflammation" by Zhang, et al., The Journal of Biological Chemistry, vol. 277, No. 48, Nov. 29, 2002, pp. 46116-46122.

* cited by examiner

ASSESSING THE RISK OF A MAJOR ADVERSE CARDIAC EVENT IN PATIENTS WITH CHEST PAIN

PRIORITY CLAIM

This application claims priority to U.S. Provisional Patent Application Ser. No. 60/513,490 filed on Oct. 22, 2003, which is incorporated herein by reference in its entirety.

STATEMENT ON FEDERALLY FUNDED RESEARCH

This invention is supported, at least in part, by, by Grant No. RO1 HL62526-01 from the National Institutes of Health. The United States government has certain rights in this invention.

BACKGROUND OF THE INVENTION

Clinical, electrocardiographic criteria, and conventional laboratory testing have been used to evaluate patients who experience chest pain. However, these procedures do not adequately predict risk of experiencing an adverse cardiac event for patients presenting with acute coronary syndromes. The use of C-reactive protein and other biomarkers have been advocated to more accurately gauge risk, but additional prognostic tools predicting coronary artery vulnerability for near-term subsequent major events in patients who present with suspected acute coronary syndromes are needed.

Creatinine kinase isoenzymes and/or cardiac troponins, are used as diagnostic biomarkers of myocardial necrosis in patients who present with chest pain.[4,5] However, many patients who present with chest pain have normal levels of creatinine kinase isoenzymes or troponins, but subsequently experience a myocardial infarction, require revascularization, or die in the ensuing 6 months. Accordingly, additional biochemical markers for determining whether a patient who presents with chest pain is at risk of experiencing a major adverse cardiac event are required. Biochemical markers that can be used to determine whether a patient who presents with chest pain is at risk of requiring medical intervention near term, e.g. within the next one to six months are especially desirable.

SUMMARY OF THE INVENTION

The present invention provides methods of determining whether a patient who presents with chest pain is at risk near term of experiencing a major adverse cardiac event, including, but not limited to, myocardial infarction, reinfarction, or death. The present invention also provides methods of determining whether a patient who presents with chest pains is at risk near term of requiring medical intervention, including but not limited to, urgent cardiac catherization, stress testing, coronary pulmonary bypass surgery, revascularization, etc.

In one embodiment, the method comprises determining the level of MPO activity in blood or a derivative thereof, including but not limited to, leukocytes, neutrophils, monocytes, serum, or plasma of a patient who presents with chest pain. The level of MPO activity in the patient's blood is then compared to a control value that is derived from measurements of MPO activity in comparable bodily samples obtained from a control population, such as the general population, or a select population of human subjects, such as patients who have presented with chest pain but who have not experienced a major adverse cardiac event within 6 months after presenting with chest pain. Such comparison is then used to characterize the patient's risk of experiencing a major adverse cardiac event, such as a myocardial infarction, reinfarction, the need for revascularization, or death. The present invention is particularly useful for characterizing the patient's risk of experiencing such a major adverse cardiac event near term, e.g. within the following 1 to 6 months. For example, patients whose blood levels of MPO activity are higher than the control value are at greater risk of experiencing a major cardiac event than patients whose blood MPO activity levels are at or close to the control value. Moreover, the extent of the difference between the patient's MPO activity levels and control value is also useful for characterizing the extent of the risk and for determining which patients would most greatly benefit from certain medical interventions, such as revascularization.

In another embodiment, the method comprises determining the level of MPO mass in a bodily sample obtained from the patient who is presenting with chest pain. The bodily sample is blood or a derivative thereof, including but not limited to, leukocytes, neutrophils, monocytes, serum, or plasma. Levels of MPO mass in bodily samples from the patient are then compared to a control value that is derived from measurements of MPO mass in comparable bodily samples obtained from a control population as, such as the general population, or a select population of human subjects, such as patients who have presented with chest pain but who have not experienced a major cardiac event within 6 months after presenting with chest pain.

In another embodiment, the method comprises determining the level of one or more select MPO-generated oxidation products in a bodily sample obtained from the test subject. The select MPO-generated oxidation products are dityrosine, nitrotyrosine, chlorotyrosine, methionine sulphoxide, and MPO-generated lipid peroxidation products. MPO lipid peroxidation products include, but are not limited to, hydroxy-eicosatetraenoic acids (HETEs); hydroxy-octadecadienoic acids (HODEs); $F_2$Isoprostanes; the glutaric and nonanedioic monoesters of 2-lyso phosphatidylcholine (G-PC and ND-PC, respectively); the 9-hydroxy-10-dodecenedioic acid and 5-hydroxy-8-oxo-6-octenedioic acid esters of 2-lysoPC(HD-diA-PC and HOdiA-PC, respectively); the 9-hydroxy-12-oxo-10-dodecenoic acid and 5-hydroxy-8-oxo-6-octenoic acid esters of 2-lysoPC(HODA-PC and HOOA-PC, respectively); the 9-keto-12-oxo-10-dodecenoic acid and 5-keto-8-oxo-6-octenoic acid esters of 2-lysoPC (KODA-PC and KOOA-PC, respectively); the 9-keto-10-dodecendioic acid and 5-keto-6-octendioic acid esters of 2-lysoPC (KDdiA-PC and KOdiA-PC, respectively); the 5-oxovaleric acid and 9-oxononanoic acid esters of 2-lysoPC (OV-PC and ON-PC, respectively); 5-cholesten-5α, 6α-epoxy-3β-ol (cholesterol α-epoxide); 5-cholesten-5β, 6β-epoxy-3β-ol (cholesterol β-epoxide); 5-cholesten-3β,7β-diol (7-OH-cholesterol); 5-cholesten-3β, 25-diol (25-OH cholesterol); 5-cholesten-3β-ol-7β-hydroperoxide (7-OOH cholesterol); and cholestan-3β, 5α, 6β-triol (triol). The bodily sample is blood, urine or a blood derivative, including but not limited to, leukocytes, neutrophils, monocytes, serum, or plasma. Levels of the selected MPO-generated oxidation products in bodily samples from the patient who presents with chest pain are then compared to a control value or control range of values that is derived from measurements of the selected MPO-generated oxidation products in comparable bodily samples obtained from a control population, such as the general population, or a select population of human subjects, such as patients who have presented with chest pain but who have not experienced a major cardiac event within 6 months after presenting with chest pain.

Also provided are kits which are employed in the present methods.

DETAILED DESCRIPTION OF THE INVENTION

Figure 1:
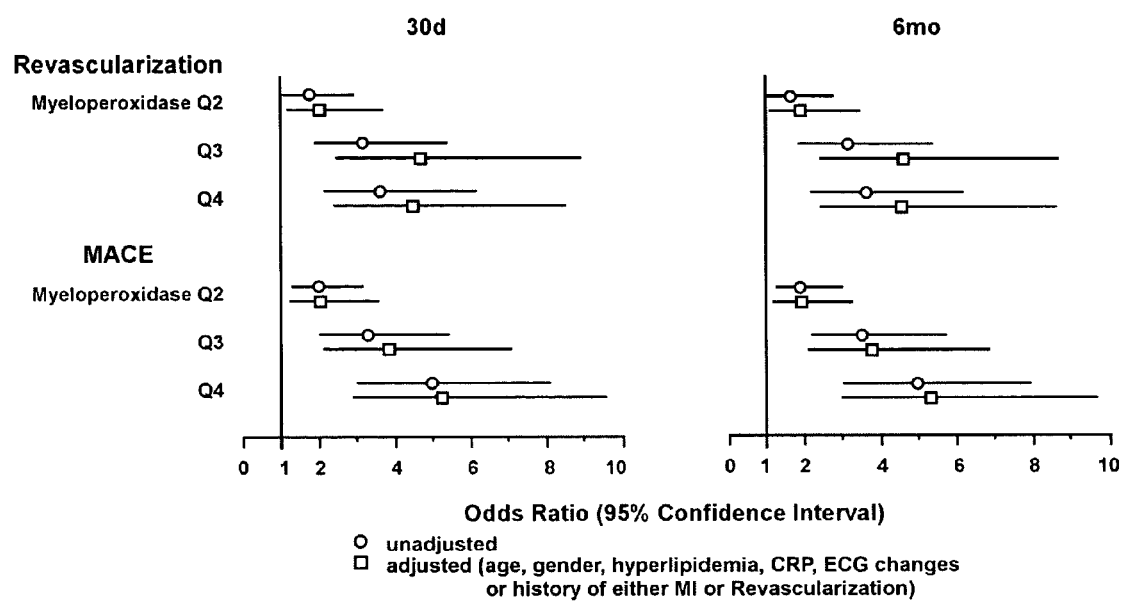
FIG. 1. Risks for Cardiovascular Outcomes in Troponin Negative Patients Based Upon Baseline Myeloperoxidase Levels. Myeloperoxidase odds ratios and 95 percent confidence intervals for revascularization and major adverse cardiac outcomes in the ensuing 30 days and 6 months following presentation are shown. (circle) Unadjusted odds ratio associated with each myeloperoxidase quartile; (square) adjusted odds ratio (for age, gender, C-reactive protein level and history of hyperlipidemia, history of revascularization, history of myocardial infarction, and ECG changes consistent with diagnosis of acute coronary syndrome) are shown.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to that this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The disclosure of all patents, patent applications (and any patents that issue thereon, as well as any corresponding published foreign patent applications), GenBank and other accession numbers and associated data, and publications mentioned throughout this description are hereby incorporated by reference herein. It is expressly not admitted, however, that any of the documents incorporated by reference herein teach or disclose the present invention.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

Provided herein are methods for assessing the near term risk of experiencing a major cardiac event in a patient with chest pain. Provided herein are methods for determining whether a patient presenting with chest pain is at near term risk of requiring medical intervention, such as revascularization. In one embodiment, the method comprises obtaining the level of MPO activity in a blood sample obtained from the patient presenting with chest pain. In another embodiment, the method comprises obtaining the level of MPO mass in a bodily sample from the patient presenting with chest pain. In another embodiment, the method comprises obtaining the level of one or more select MPO-generated oxidation products in a bodily sample from the patient presenting with chest pain. Such MPO-generated oxidation products are selected from the group consisting of dityrosine, nitrotyrosine, methionine sulphoxide, chlorotyrosine and a lipid peroxidation product. In yet another embodiment, the method comprises obtaining the level of MPO activity, or MPO mass, or both, and the level of one or more select MPO-generated oxidation products in a bodily sample obtained from the patient.

The level of the selected risk predictor, i.e., MPO activity, MPO mass, MPO-generated oxidation product, or combinations thereof, in the patient's bodily sample is then compared to a control value or range of control values that is based on the level of the same risk predictor in a comparable bodily sample of individuals in a control population. Such comparison provides information which characterizes the patient's risk near term of experiencing a major adverse cardiac event such as myocardial infarction, or death. The difference between the level of risk predictor in the bodily sample of the patient and the level of the risk predictor in a bodily sample from individuals in the control population also provides information about the extent of the risk. Thus, the level of MPO or MPO-generated oxidation product in the blood of a patient presenting with chest pain can be used to identify patients in need of more aggressive carepath and global risk reduction therapies, such as more urgent cardiac catherization or stress testing before being discharged to follow up with the patient's primary care physician.

The present invention also relates to kits that comprise assays for MPO activity or mass, or the select MPO-generated oxidation product. Such assays have appropriate sensitivity with respect to control values selected on the basis of the present predictive tests. The present kits differ from those presently commercially available for MPO by including, for example, different cut-offs, different sensitivities at particular cut-offs, as well as instructions or other printed material for characterizing the patient's risk of experiencing a major adverse cardiac event near term based upon the outcome of the assay.

Preparation of Bodily Sample

Whole blood is obtained from the patient using standard clinical procedures. Plasma is obtained from whole blood samples by centrifugation of anti-coagulated blood. Such process provides a buffy coat of white cell components and a supernatant of the plasma.

Serum is collected by centrifugation of whole blood samples that have been collected in tubes that are free of anti-coagulant. The blood is permitted to clot prior to centrifugation. The yellowish-reddish fluid that is obtained by centrifugation is the serum.

Leukocytes can be isolated from whole blood samples by any of various techniques including buoyant density centrifugation as described in the examples below.

Methods of Determining MPO Activity

MPO (donor: hydrogen peroxide, oxidoreductase, EC 1.11.1.7) is a tetrameric, heavily glycosylated, basic (PI. 10) heme protein of approximately 150 kDa. It is comprised of two identical disulfide-linked protomers, each of which possesses a protoporphyrin-containing 59-64 kDa heavy subunit and a 14 kDa light subunit (Nauseef, W. M, et al., *Blood* 67:1504-1507; 1986.)

Myeloperoxidase activity may be determined by any of a variety of standard methods known in the art. One such method is a colorimetric-based assay where a chromophore that serves as a substrate for the peroxidase generates a product with a characteristic wavelength which may be followed by any of various spectroscopic methods including UV-visible or fluorescence detection. Additional details of colorimetric based assays can be found in Kettle, A. J. and Winterboum, C. C. (1994) *Methods in Enzymology.* 233: 502-512; and Klebanoff, S. J., Waltersdorph, A. N. and Rosen, H. (1984) *Methods in Enzymology.* 105: 399-403, both of which are incorporated herein by reference. An article by Gerber, Claudia, E. et al, entitled "Phagocytic Activity and Oxidative Burst of Granulocytes in Persons with Myeloperoxidase Deficiency" published in 1996 in Eur. J. Clin. Chem. Clin Biochem 34:901-908, describes a method for isolation for polymorphonuclear leukocytes (i.e. neutrophils) and measurement of myeloperoxidase activity with a colorometric assay, which involves oxidation of the chromgen 4-chloro-1-naphthol.

Peroxidase activity may be determined by in situ peroxidase staining in MPO containing cells with flow cytometry-based methods. Such methods allow for high through-put screening for peroxidase activity determinations in leukocytes and subpopulations of leukocytes. An example is the cytochemical peroxidase staining used for generating white blood cell count and differentials with hematology analyzers based upon peroxidase staining methods. For example, the Advia 120 hematology system by Bayer analyzes whole blood by flow cytometry and performs peroxidase staining of white blood cells to obtain a total white blood cell count (CBC) and to differentiate amongst the various white blood cell groups.

With these methods, whole blood enters the instrument and red blood cells are lysed in a lysis chamber. The remaining white blood cells are then fixed and stained in situ for peroxidase activity. The stained cells are channeled into the flow cytometer for characterization based upon the intensity of peroxidase staining and the overall size of the cell, which is reflected in the amount of light scatter of a given cell. These two parameters are plotted on the x and y axis, respectively, by conventional flow cytometry software, and clusters of individual cell populations are readily discernible. These include, but are not limited, to neutrophils, monocytes and eosinophils, the three major leukocyte populations containing visible peroxidase staining.

During the course of these analyses, leukocytes such as monocytes, neutrophils, eosinophils and lymphocytes are identified by the intensity of peroxidase staining and their overall size. Information about the overall peroxidase activity staining within specific cell populations is thus inherent in the position of individual cell clusters (e.g. neutrophil, monocyte, eosinophil clusters) and peroxidase levels within specific cell populations may be determined. Peroxidase activity/staining in this detection method is compared to a peroxidase stain reference or calibrant. Individuals with higher levels of peroxidase activity per leukocyte are identified by having a cell population whose location on the cytogram indicates higher levels of peroxidase (i.e., average peroxidase activity per leukocyte) or by demonstrating a sub-population of cells within a cell cluster (e.g. neutrophil, monocyte, eosinophil clusters) which contain higher levels of peroxidase activity either on average or in a higher subgroup, such as the higher tertile or quartile.

Methods of Determining MPO Mass

The mass of myeloperoxidase in a given sample is readily determined by an immunological method, e.g. ELISA. Commercial kits for MPO quantification by ELISA are available.

MPO mass in a sample can also be determined indirectly by in situ peroxidase staining of the bodily sample. Methods which analyze leukocyte peroxidase staining can be performed on whole blood, such as those with hematology analyzers which function based upon in situ peroxidase staining. Previous studies by other investigators have demonstrated that the overall intensity of staining is proportional to peroxidase mass (e.g. Claudia E. Gerber, Selim Kuci, Matthias Zipfel, Ditrich Niethammer and Gernot Bruchfelt, "Phagocytic activity and phagocytic activity and oxidative burst of granulocytes in persons with myeloperoxidase deficiency" European Journal of Clinical Chemistry and Clinic Biochemistry (1996) 34: 901-908).

Flow cytometry through a hematology analyzer is a high through-put technique for quantifying the parameters used in determining MPO activity or mass levels or numbers of cells containing elevated levels of MPO activity or mass. The advantage of using such a technique is its ease of use and speed. The Advia 120 can perform 120 complete cell blood count and differentials in one hour and utilizes only a few microliters of blood at a time. All the data necessary for determination of the peroxidase activity is held within the flow cytometry cell clusters used to ultimately calculate the total white blood cell count and differential. With minor adjustments to software of this apparatus, the readout can be modified to include multiple different indices of overall peroxidase activity. For example, patients presenting with chest pain whose neutrophil clusters contain an overall increase in the average peroxidase activity (i.e. increased mean peroxidase index) will be at increased risk for experiencing a major adverse cardiac event. In addition to simply determining the mean peroxidase activity for a given cell type, individuals at increased risk of experiencing a major adverse cardiac event can be identified by examining the overall distribution of peroxidase activity within a given cell cluster (mean+mode, etc). It is expected that by looking at the population of peroxidase activity per leukocyte, patients who possess leukocytes with a higher proportion of cells containing a high peroxidase activity in a subset of cells (for example, the upper quartile, or the upper tertile) may be at particularly high risk.

Levels of MPO Activity and MPO Mass

The level of MPO activity or MPO mass in the body fluid can be determined by measuring the MPO activity or MPO mass in the body fluid and normalizing this value to obtain the MPO activity or mass per ml of blood, per ml of serum, per ml of plasma, per leukocyte (e.g. neutrophil or monocyte), per weight, e.g. mg of total blood protein, per weight of leukocyte protein (e.g. per weight of neutrophil or monocyte protein). Alternatively, the level of MPO activity or MPO mass in the body fluid can be a representative value which is based on MPO activity in the test subjects blood or blood derivatives. For example the level of MPO activity can be the percentage or the actual number of the test subject's neutrophils or monocytes that contain elevated levels of MPO activity or MPO mass. Examples of other representative values include, but are not limited to, arbitrary units for a parameter that can be obtained from a flow cytometry based cytogram, such as the position of the neutrophil cluster on the X and Y axes, or the angle of the major axis of the neutrophil cluster relative to the X and Y axes.

Methods of Determining Levels of Select Myeloperoxidase-Generated Oxidation Products Dityrosine and Nitrotyrosine Dityrosine and nitrotyrosine levels in the bodily sample can be determined using monoclonal antibodies that are reactive with such tyrosine species. For example, anti-nitrotyrosine antibodies may be made and labeled using standard procedures and then employed in immunoassays to detect the presence of free or peptide-bound nitrotyrosine in the sample. Suitable immunoassays include, by way of example, radioimmunoassays, both solid and liquid phase, fluorescence-linked assays or enzyme-linked immunosorbent assays. Preferably, the immunoassays are also used to quantify the amount of the tyrosine species that is present in the sample.

Monoclonal antibodies raised against the dityrosine and nitrotyrosine species are produced according to established procedures. Generally, the dityrosine or nitrotyrosine residue, which is known as a hapten, is first conjugated to a carrier protein and used to immunize a host animal. Preferably, the dityrosine and nitrotyrosine residue is inserted into synthetic peptides with different surrounding sequence and then coupled to carrier proteins. By rotating the sequence surrounding the dityrosine and nitrotyrosine species within the peptide coupled to the carrier, antibodies to only the dityrosine and nitrotyrosine species, regardless of the surrounding sequence context, are generated. Similar strategies have been successfully employed with a variety of other low molecular weight amino acid analogues.

Suitable host animals, include, but are not limited to, rabbits, mice, rats, goats, and guinea pigs. Various adjuvants may be used to increase the immunological response in the host animal. The adjuvant used depends, at least in part, on the host species. To increase the likelihood that monoclonal antibodies specific to the dityrosine and nitrotyrosine are produced, the peptide containing the respective dityrosine and nitrotyrosine species may be conjugated to a carrier protein which is present in the animal immunized. For example, guinea pig albumin is commonly used as a carrier for immunizations in guinea pigs. Such animals produce heterogenous populations of antibody molecules, which are referred to as polyclonal antibodies and which may be derived from the sera of the immunized animals.

Monoclonal antibodies, which are homogeneous populations of an antibody that binds to a particular antigen, are obtained from continuous cells lines. Conventional techniques for producing monoclonal antibodies are the hybridoma technique of Kohler and Millstein (Nature 356:495-497 (1975)) and the human B-cell hybridoma technique of Kosbor et al (Immunology Today 4:72 (1983)). Such antibodies may be of any immunoglobulin class including IgG, IgM, IgE, Iga, IgD and any class thereof. Procedures for preparing antibodies against modified amino acids, such as for example, 3-nitrotyrosine are described in Ye, Y. Z., M. Strong, Z. Q. Huang, and J. S. Beckman. 1996. Antibodies that recognize nitrotyrosine. *Methods Enzymol.* 269:201-209.

In general, techniques for direct measurement of protein bound dityrosine and nitrotyrosine species from bodily fluids involves removal of protein and lipids to provide a fluid extract containing free amino acid residues. The tissues and bodily fluids are stored, preferably in buffered, chelated and antioxidant-protected solutions, preferably at −80° C. as described above. The frozen tissue, and bodily fluids are then thawed, homogenized and extracted, preferably with a single phase mixture of methanol:diethylether:water as described above to remove lipids and salts. Heavy isotope labeled internal standards are added to the pellet, which, preferably, is dried under vacuum, hydrolyzed, and then the amino acid hydrolysate resuspended, preferably in a water:methanol mixture, passed over a mini solid-phase C18 extraction column, derivatized and analyzed by stable isotope dilution gas chromatography-mass spectrometry as above. Values of free dityrosine and nitrotyrosine species in the bodily sample can be normalized to protein content, or an amino acid such as tyrosine as described above.

In a highly preferred procedure, protein is delipidated and desalted using two sequential extractions with a single phase mixture of $H_2O$/methanol/$H_2O$-saturated diethyl ether (1:3:8 v/v/v). Oxidized tyrosine standards (2 pmol each) and universal labeled tyrosine (2 nmol) are added to protein pellets. Proteins are hydrolyzed by incubating the desalted protein pellet with degassed 6N HCl supplemented with 1% phenol for 24 h under argon atmosphere. Amino acid hydrolysates are resuspended in chelex treated water and applied to mini solid-phase C18 extraction columns (Supelclean LC-C18SPE minicolumn; 3 ml; Supelco, Inc., Bellefone, Pa.) pre-equilibrated with 0.1% trifluoroacetic acid. Following sequential washes with 2 ml of 0.1% trifluoroacetic acid, oxidized tyrosines and tyrosine are eluted with 2 ml 30% methanol in 0.1% trifluoroacetic acid, dried under vacuum and then analyzed by mass spectrometry.

Tandem mass spectrometry is performed using electrospray ionization and detection with an ion trap mass spectrometer (LCQ Deca, ThermoFinigann, San Jose, Calif.) interfaced with a Thermo SP4000 high performance liquid chromatograph (HPLC). Samples are suspended in equilibration solvent ($H_2O$ with 0.1% formic acid) and injected onto a Ultrasphere C18 column (Phenominex, 5 μm, 2.0 mm×150 mm). L-Tyrosine and its oxidation products are eluted at a flow rate of 200 μl/min using a linear gradient generated against 0.1% formic acid in methanol, pH 2.5 as the second mobile phase. Analytes are monitored in positive ion mode with full scan product ion MS/MS at unit resolution. Response is optimized with a spray voltage setting of 5 KV and a spray current of 80 μA. The heated capillary voltage is set at 10 V and the temperature to 350° C. Nitrogen is used both as sheath and auxiliary gas, at a flow rate of 70 and 30 arbitrary units, respectively. The analyte abundance is evaluated by measuring the chromatographic peak areas of selected product ions extracted from the full scan total ion chromatograms, according to the corresponding ion trap product ion spectra. The ions monitored for each analyte are: 3-nitro[$^{12}C_6$]tyrosine (mass-to-charge-ratio (m/z) 227, 181 and 210), 3-nitro[$^{13}C_6$]tyrosine (m/z 233, 187 and 216), 3-nitro[$^{13}C_9^{15}N_1$]tyrosine (m/z 237, 190 and 219), [$^{12}C_6$]tyrosine (m/z 182, 136 and 165), [$^{13}C_9^{15}N_1$]tyrosine (m/z 192, 145 and 174). Tyrosine and nitrotyrosine are base-line resolved under the HPLC conditions employed, permitting programming of the LCQ Deca for analysis over 0-7 min for detection of tyrosine isotopomers, and from 7 min on for detection of 3-nitrotyrosine isotopomers.

Free nitrotyorsine and dityrosine are similarly measured in samples, but tissue or bodily fluid is first passed through a low molecular weight cut off filter and the low molecular weight components analyzed by LC/ECS/MS/MS. Values of free and protein-bound dityrsoine and nitrotyrosine species in the bodily sample can be normalized to protein content, or an amicon acid such as the precursor tyrosine, as described below.

Lipid Oxidation Products

Lipid oxidation products can be measured by HPLC with UV detection or HPLC with on line mass spectrometry. Other analytical methods including GC/MS and immunocytochmeical methods may also be used. $F_2$Isoprostanes are measurable by various mass spectrometry techniques as known in the art.

Methods of extracting and quantifying the MPO-generated lipid oxidation products hydroxy-eicosatetraenoic acids (HETEs), hydroxy-octadecadienoic acids (HODEs), F2Isoprostanes; the 5-oxovaleric acid esters of 2-lysoPC (OV-PC); 5-cholesten-5α,6α-epoxy-3β-ol (cholesterol α-epoxide); 5-cholesten-5β, 6β-epoxy-3β-ol (cholesterol β-epoxide); 5-cholesten-3β,7β-diol (7-OH-cholesterol); 5-cholesten-3β, 25-diol (25-OH cholesterol 5-cholesten-3β-ol-7β-hydroperoxide (7-OOH cholesterol); and cholestan-3β, 5α, 6β-triol (triol) are described in Schmitt, et al. (1999) Biochemistry, Vol. 38, 16904-16915, which is specifically incorporated herein by reference. For determination of 9-H(P)ODE, 9-H(P)ETE and $F_2$-isoprostanes, hydroperoxides in reaction mixtures are reduced to their corresponding hydroxides during extraction utilizing a modified Dole procedure in which the reducing agent, triphenylphosphine, is present (Savenkova, M. L., et al. (1994) *J. Biol. Chem.* 269, 20394-20400). These conditions also inhibit artifactual formation of isoprostanes and oxidized lipids. Lipids are dried under $N_2$, resuspended in isopropanol (2 ml) and then fatty acids released by base hydrolysis with 1 N sodium hydroxide (2 ml) at room temperature under $N_2$ for 90 min. The samples are acidified (pH 3.0) with 2N HCl, known amounts of internal standards are added and free fatty acids are extracted twice with hexane (5 ml). The content of 9-H(P)ODEs, 9-H(P)ETEs and $F_2$-isoprostanes are then determined by LC/MS/MS analysis as outlined below.

1-palmitoyl-2 oxovaleryl-sn-glycero-3-phosphatidyl choline (PoxvPC) is extracted by the same modified Dole procedure used for 9-H(P)ODE, 9-H(P)ETE and $F_2$ isoprostane analyses as above, but omitting addition of the reductant, triphenylphosphine. Lipids are dried under $N_2$, resuspended in methanol and stored under argon at −70° C. until subsequent LC/MS analysis as outline below. Sterol oxidation products are extracted by adding 4 M NaCl (150 μl) and acetonitrile (500 μl). Samples are vortexed, centrifuged, and the upper organic phase removed. Extracts are dried under $N_2$, resuspended in methanol, and stored under argon at −70° C. until analysis by HPLC with on-line mass spectrometric analysis.

Mass spectrometric analyses are performed on a Quatro II triple quadruple mass spectrometer interfaced with an HP 1100 HPLC. $F_2$-isoprostanes are quantified by stable isotope dilution mass spectrometry using on-line reverse phase HPLC tandem mass spectrometry (LC/MS/MS) with 8-epi-[$^2H_4$]PGF$_{2α}$ as standard as described by Mallat (Mallat, Z., et al. (1999) *J. Clin. Invest.* 103, 421-427). For 9-HODE and 9-HETE analyses, lipid extracts generated following base hydrolysis of reduced lipids (above) are dried under $N_2$ and reconstituted in methanol. An aliquot of the mixture is then injected on an Ultrasphere ODS C18 column equilibrated and run under isocratic conditions employing methanol:$H_2O$, (85:15, v/v) as solvent. Column eluent is split (930 μl/min to UV detector and 70 μl/min to mass detector) and analyzed by the mass spectrometer. LC/MS/MS analysis of 9-HODE, 9-HETE and $F_2$-isoprostanes in column effluents is performed using electrospray ionization mass spectrometry (ESI-MS) in the negative-ion mode with multiple reaction monitoring (MRM) and monitoring the transitions m/z 295→171 for 9-HODE; m/z 319→151 for 9-HETE; m/z 353→309 for $F_2$-isoprostanes; and m/z 357→313 for [$^2H_4$] PGF$_{2α}$.

Quantification of POxvPC is performed on lipid extracts utilizing HPLC with on-line ESI-MS analysis in the positive ion mode and selected ion monitoring at m/z 782 and m/z 594, respectively. An aliquot of lipid extract reconstituted in methanol (above) is mixed 0.1% formic acid in methanol (mobile phase B) and loaded onto a Columbus C18 column (1×250 mm, 5 μm, P. J. Cobert, St. Louis, Mo.) pre-equilibrated in 70% mobile phase B, 30% mobile phase A (0.1% formic acid in water) at a flow rate of 30 μl/min. Following a 3 min wash period at 70% mobile phase B, the column is developed with a linear gradient to 100% mobile phase B, followed by isocratic elution with 100% mobile phase B. External calibration curves constructed with authentic POxvPC are used for quantification. 7-OH cholesterol, 7-keto cholesterol, and 7-OOH cholesterol are resolved on an Ultrasphere ODS C18 column. The elution gradient consisted of 91:9, acetonitrile:water+0.1% formate (v:v), and the column washed between runs with acetonitrile+0.1% formate. Column effluent is split (900 μl/min to UV detector and 100 μl/min to mass detector) and ionized by atmospheric pressure chemical ionization (APCI) in the positive-ion mode with selected ion monitoring. Identification of 7-OH cholesterol is performed by demonstrating co-migration of ions with m/z 385.3 (M−$H_2O$)$^+$ and m/z 367.3 (M−$2H_2O$)$^+$ with the same retention time as authentic standard. The integrated area of the ion current for the peak monitored at m/z 367.3 is used for quantification. Identification of 7-OOH cholesterol ois performed by demonstrating co-migration of ions with m/z 401.3 (M−$H_2O$)$^+$, m/z 383.3 (M−$2H_2O$)$^+$ and m/z 367.3 (M−$H_2O_2$)$^+$ with the same retention time as authentic standard. The integrated area of the ion current for the peak monitored at m/z 401.3 is used for quantification. Identification of 7-keto cholesterol is performed by demonstrating co-migration of ions with m/z 401.3 (M+H)$^+$ and m/z 383.3 (M−$H_2O$)$^+$ with the same retention time as authentic standard. The integrated area of the ion current for the peak monitored at m/z 401.3 is used for quantification. External calibration curves constructed with authentic 7-OH cholesterol, 7-OOH cholesterol and 7-keto cholesterol are used for quantification following preliminary APCI LC/MS experiments demonstrating identical results to those obtained by the method of standard additions. The retention times for 25-OH cholesterol, 5,6 α- and β-epoxides, and triol are determined by LC/MS analysis of authentic standards.

Control Value

The level of MPO mass, MPO activity, or select MPO-generated oxidation product in the bodily sample obtained from the test subject is compared to a control value or range of values. The control value or range of values is based upon the levels of MPO activity, MPO mass, or select MPO-generated oxidation product in comparable samples obtained from a control population, such as the general population or a select population of human subjects. For example, the select population may be comprised of apparently healthy subjects. "Apparently healthy", as used herein, means individuals who have not previously had any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography. Apparently healthy individuals also do not otherwise exhibit symptoms of disease. In other words, such individuals, if examined by a medical professional, would be characterized as healthy and free of symptoms of disease. In another embodiment, the control population may be a population of test subjects who have presented with chest pain but who have not experienced a major cardiac event within 6 months of presenting with chest pain.

The control value is related to the value used to characterize the level of MPO activity or MPO mass in the bodily sample obtained from the test subject. Thus, if the level of MPO activity is an absolute value such as the units of MPO activity per leukocyte or per ml of blood, the control value is also based upon the units of MPO activity per leukocyte or per ml of blood in individuals in the control population. Similarly, if the level of MPO activity or MPO mass is a representative value such as an arbitrary unit obtained from a cytogram, the control value or range of values is also based on the representative value.

The control value can take a variety of forms. The control value can be a single cut-off value, such as a median or mean. The control value can be established based upon comparative groups such as where the risk in one defined group is double the risk in another defined group. The control value can be a control range of values, for example, where the general population is divided equally (or unequally) into groups, such as a low risk group, a medium risk group and a high-risk group, or into quadrants, the lowest quadrant being individuals with the lowest risk the highest quadrant being individuals with the highest risk.

The control value can be derived by determining the level of MPO activity or mass in the general population. Alternatively, the control value can be derived by determining the level of MPO activity or mass in a select population, such as an apparently healthy nonsmoker population. For example, an apparently healthy, nonsmoker population may have a different normal range of MPO activity or MPO mass than will a smoking population or a population whose member have had a prior cardiovascular disorder. Accordingly, the control values selected may take into account the category in which an individual falls. Appropriate ranges and categories can be selected with no more than routine experimentation by those of ordinary skill in the art.

Control values of MPO activity or MPO mass, such as for example, mean levels, median levels, or "cut-off" levels, are established by assaying a large sample of individuals in control population or populations and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed. The standardized method that was used in Example 1 below employs the guaiacol oxidation assay as described in Klebanoff, S. J., Waltersdorph, A. N. and Rosen, H. 1984. "Antimicrobial activity of myeloperoxidase". Methods in Enzymology. 105: 399-403).

By selecting the appropriate control population, sample size, and statistical model, one can obtain a control value that enables one to assess the risk of the patient experiencing a major adverse cardiac event within a time period of days to months following the chest pain. Thus, the present method can be used to assess the patient's risk of experiencing a major cardiac event within one month, two months, three months, four months, five months, six months, etc. of experiencing the chest pain.

Comparison of MPO Activity and Mass Levels and Levels of Select MPO-Generated Oxidation Products in the Bodily Sample from the Patient Presenting with Chest Pain to the Control Value.

The levels of each risk predictor, i.e., MPO activity, MPO mass and select MPO-generated oxidation product, in a bodily sample from the patient presenting with chest pain may be compared to a single control value or to a range of control values. If the level of the present risk predictor in the bodily sample of the patient presenting with chest is greater than the control value or range of control values, the patient is at greater risk of experiencing a major adverse cardiac event than other patients presenting with chest pain whose risk predictor levels are comparable to or below the control value or at the lower end of the control range of values. In contrast, if the level of the present risk predictor in the bodily sample of the patient presenting with chest pain is below the control value or at the lower end of the range of control values, the patient presenting with chest pain is at a lower risk of requiring aggressive medical intervention that patients presenting with chest pain whose levels of the select risk predictor are comparable to or above the control value or at the upper end of the range of control values. For example, a patient presenting with chest pain who has a much higher number of neutrophils or monocytes or both with elevated levels of MPO activity or MPO mass as compared to the control value is at high risk of experiencing a major adverse cardiac event, and a patient presenting with chest pain who has a lower number of neutrophils or monocytes or both with decreased or lower levels of MPO activity or MPO mass as compared to the control value is at low risk of experiencing a major adverse cardiac event near term. The extent of the difference between the test subject's risk predictor levels and control value is also useful for characterizing the extent of the risk and thereby, determining which individuals would most greatly benefit from certain aggressive therapies. In those cases, wherein the control value ranges are divided into a plurality of groups, such as the control value ranges for individuals at high risk, average risk, and low risk, the comparison involves determining into which group the patient's level of the relevant risk predictor falls.

The present tests are useful for determining if and when patients presenting with chest pain should be further evaluated, such as being subjected to a stress tests or angiography, or should be scheduled for medical intervention before being discharged to the care of their primary care physician. For example, patients whose values of MPO activity (U/mg PMN protein; or U/ml blood) are above a certain cutoff value, or are in the higher tertile or quartile of a "normal range," could be identified as those in need of more extensive follow-ups or aggressive intervention such as coronary bypass surgery (CABG), percutaneous coronary intervention or positive catherization.

EXAMPLES

The following examples are for purposes of illustration only and are not intended to limit the scope of the claims which are appended hereto.

Methods

Study Design: Recruitment occurred as part of a study comparing troponin-T vs. creatine kinase-MB isoform for the diagnosis of myocardial infarction.[21] Patients presenting to the Emergency Department with chest pain of suspected cardiac origin within 24 hours of onset were eligible.

Clinical Diagnosis: Myocardial infarction was defined by positive troponin-T ($\geq$0.1 ng/ml). Unstable angina was ascertained based on the presence of angina at rest, sudden increase in episodes of previously stable angina, ST segment depression, or T wave inversions, as described.[21] ECG data were verified independently by blinded ECG core facility personnel. Diagnosis of acute coronary syndrome was adjudicated based on myocardial infarction or unstable angina, as defined by protocol, and confirmed by chart review by a blinded investigator.

Outcome Definitions: Patients were assessed for major adverse cardiac outcomes (myocardial infarction, reinfarction, need for revascularization, and death). Medical record review and follow up phone interviews were performed for 30 day and 6 month outcomes. Need for revascularization was defined as undergoing coronary artery bypass surgery, percutaneous coronary intervention or positive catheterization with $\geq$2 lesions with >70% stenosis.

Healthy Volunteers: Sequential subjects responding to advertisements in a community newspaper were recruited. Subjects (age $\geq$21y) without history or clinical evidence of coronary artery disease were eligible to participate. Population characteristics were: age (49±12.4y), male gender (54.8%), family history of coronary artery disease (44.3%), current smoking (36.5%) or history of diabetes (2.6%), hypertension (22.6%), or hyperlipidemia (69.6%). The Institutional Review Board at the Cleveland Clinic Foundation approved the study protocol.

Biochemical Analyses: Troponin-T measures were performed on an ES300 analyzer (Boehringer Mannheim, Indianapolis, Ind.). Baseline myeloperoxidase levels were measured by ELISA (OXIS, Intl., Portland, Oreg.). Each plate included a standard curve with isolated myeloperoxidase (extinction coefficient of 178,000 $M^{-1}cm^{-1}$; ref. 22) and controls to correct for interplate variability. High sensitivity C-reactive protein measures were determined by nephelometry (Dade Behring, Deerfield, Ill.). Creatine kinase-MB mass was measured by immunoassay (Abbott Laboratories, Abbott Park, Ill.).

Statistical Analysis: Patient characteristics are presented as either mean (SD) or median (IQR) for continuous measures and as number (percentage) for categorical measures. Differences between outcome groups and associations among categorical variables were assessed with Wilcoxon Rank Sum test. Unadjusted trends were evaluated with the Cochran-Armitage trend test. Correlations among continuous variables were assessed with Spearman rank-correlation coefficient. Multivariate logistic regression models (SAS version 8.0, SAS Institute, Inc., Cary, N.C.) were developed to calculate odds ratios and 95% confidence intervals.

Results

Population Characteristics

The study population consisted of 604 patients presenting to the Emergency Department with complaint of chest pain (Table 1). The mean time from chest pain to presentation was 4.0 hours. Final diagnoses included myocardial infarction (24%), unstable angina (17%), suspected coronary syndrome (37%), and non-cardiac chest pain (22%). Outcomes (30 day) included myocardial infarction (146 events), death (9), revascularization (189) and major adverse cardiac event (245).

Myeloperoxidase Levels in Healthy Volunteers and in Subjects Presenting to the Emergency Department with Chest Pain Plasma levels of myeloperoxidase in subjects presenting with chest pain ranged from 0 to 4666 pM with a median of 198 pM and an interquartile range of 119 pM to 394 pM. These levels were significantly higher than those observed in healthy volunteers (n=115; median 120 pM, interquartile range of 97 pM to 146 pM; P<0.001). Myeloperoxidase levels in patients were correlated with peak troponin-T (r=0.21, P<0.001), C-reactive protein levels (r=0.10, P=0.01), and age (r=0.11, P=0.01), but not white blood cell count (P=0.11). Myeloperoxidase levels were higher in males (median 213 pM versus 184 pM; P=0.05). Median myeloperoxidase levels did not differ by smoking status, history of diabetes, hypertension, myocardial infarction or coronary artery disease, but were significantly higher in patients with a history of either hyperlipidemia (232 pM versus 181 pM; P<0.01) or revascularization (234 pM versus 189 pM; P<0.01).

Baseline Myeloperoxidase Levels and Risks at Index Presentation

Myeloperoxidase levels were higher in patients who experienced a myocardial infarction within 16 hours of presentation (median, 320 pM versus 178 pM; P<0.001). Among patients with no biochemical evidence of significant myocardial necrosis at entry (t=0 h), baseline myeloperoxidase levels were significantly elevated in those that subsequently manifest a positive cardiac troponin-T level within the ensuing 4 to 16 hours (median, 353 pM versus 309 pM; P<0.001).

The incidence of myocardial infarction increased with increasing quartile of myeloperoxidase (quartiles 1,2,3, and 4 rates of 13.9%, 16.6%, 25.2% and 38.4%; P<0.001 for trend). Patients with initial (t=0 h) negative troponin-T levels, but subsequent (t=4-16 h) positive cardiac enzymes, were more likely to be in the $3^{rd}$ and $4^{th}$ myeloperoxidase quartiles (quartiles 1, 2, 3, and 4 rates of 5.3%, 5.3%, 8.0%, and 17.2%; P<0.001 for trend). Myeloperoxidase levels also correlated with the frequency of adjudicated diagnosis of acute coronary syndrome, increasing from 22.5% to 58.0% in quartiles 1 to 4 (P<0.001 for trend).

Baseline Myeloperoxidase Levels: 30 Day and 6 Month Outcomes

Myeloperoxidase levels at presentation were higher in patients that subsequently experienced revascularization or major adverse cardiac events (myocardial infarction, re-infarction, need for revascularization and death) in the ensuing 30 day and 6 month period (P<0.001 for all comparisons). Myeloperoxidase levels were also increased in those patients (n=34) that died within 6 months of presentation (270 pM vs. 194 pM; P=0.05).

Myeloperoxidase levels were highest in patients presenting within 4.0 to 9.6 hours following onset of symptoms (mean ±SE, 351±47 pM; P=0.041 and P=0.002 for comparisons versus subjects presenting <2.0 h or >9.6 h after onset of symptoms, respectively). Myeloperoxidase levels remained a robust predictor of outcomes across the distribution of times between onset of symptoms and time of blood draw. Moreover, plasma myeloperoxidase levels in subjects presenting <2 hours of onset of symptoms (mean ±SE, 291±32 pM) were significantly higher than those in healthy volunteers (P<0.001).

Myeloperoxidase as Independent Predictor of Short- and Near-Term Risks

Myeloperoxidase quartiles increasingly predicted risk for myocardial infarction at presentation, both for the entire cohort and for those patients with initial (t=0 h) negative troponin-T values (Table 2; p<0.001). Myeloperoxidase also predicted risk for major adverse cardiac events within 30 days and 6 months following index presentation (Table 2; p<0.001). The unadjusted odds ratio (95% confidence interval) for major adverse cardiac outcomes within 30 days and 6 months for the highest quartile of myeloperoxidase plasma levels were 4.7(2.8-7.7) at 30 days and 4.7(2.9-7.7) at 6 months, respectively (P<0.001 each). Similar odds ratios and 95% confidence intervals were observed for plasma myeloperoxidase levels as a predictor of revascularization at both 30 days and 6 months (not shown). Stratification based on gender revealed that while myeloperoxidase levels were lower in females (P=0.05), they predicted similar risks for both genders (myeloperoxidase $4^{th}$ quartile odds ratio (95 percent confidence intervals) for 30 d major adverse cardiac events of 8.3(3.4 to 20.2) for females, and 3.5(1.9 to 6.5) for males).

To ascertain whether plasma myeloperoxidase levels independently predict risk of revascularization, myocardial infarction and major adverse coronary events, multivariate logistic regression models were used. Adjustments were made for variables associated with myeloperoxidase levels or outcomes in univariate models (age, gender, C-reactive protein, history of hyperlipidemia, history of revascularization, history of prior myocardial infarction, or ECG changes consistent with acute coronary syndromes). Unadjusted versus adjusted odds ratios and 95% confidence intervals for the entire cohort were virtually identical, confirming that elevated levels of myeloperoxidase served as an independent predictor of increased risk for myocardial infarction, need for revascularization and major adverse coronary outcomes within 30 d and 6 months following presentation (P<0.001 each).

Clinical Outcomes in Troponin Negative Patients

To test whether myeloperoxidase serves not only as a marker of inflammation in response to myocardial necrosis, but also as a sensitive predictor of the vulnerable plaque, we examined whether plasma myeloperoxidase levels predicted risk among patients that present to the Emergency Department with chest pain, but in whom no evidence of myocardial necrosis is noted (i.e. troponin-T negative throughout monitoring period, t=0-16 h). Within this cohort (n=462), myeloperoxidase levels were significantly higher in patients with subsequent major adverse cardiac events in the intervening 30 days and 6 months compared to those who did not experience an event (e.g. median (interquartile range) for subjects with versus without 30 day major adverse cardiac event of 268 (152-444)pM versus 158(100-307) pM, respectively; P<0.001). Among subjects who were troponin-T negative throughout the index presentation (t=0-16 h), the frequency of 30 day and 6 month major adverse cardiac events increased with increasing myeloperoxidase quartiles (P<0.001 for each trend).

For troponin negative patients, the risk for revascularization and major adverse cardiac events at 30 days and 6 months following initial presentation increased with increasing quartiles of myeloperoxidase (Table 2). FIG. 1 illustrates adjusted and unadjusted odds ratios and 95% confidence intervals for myeloperoxidase quartiles as predictors of subsequent revascularization and major adverse cardiac events within subjects who remained troponin-T negative in the Emergency Department. Multivariate adjustment using factors associated with plasma myeloperoxidase levels and outcomes in the cohort failed to significantly alter risks, confirming that plasma levels of myeloperoxidase serve as strong and independent predictors of 30 day and 6 month risk for revascularization and major adverse coronary events (FIG. 1).

Comparison with Established Diagnostic and Prognostic Biomarkers

To evaluate whether plasma myeloperoxidase levels provide additive value to C-reactive protein levels, parallel analyses were performed for C-reactive protein levels (Table 2). C-reactive protein predicted risk for myocardial infarction at presentation, but was not predictive of major adverse cardiac events in troponin negative patients.

Figure 2:
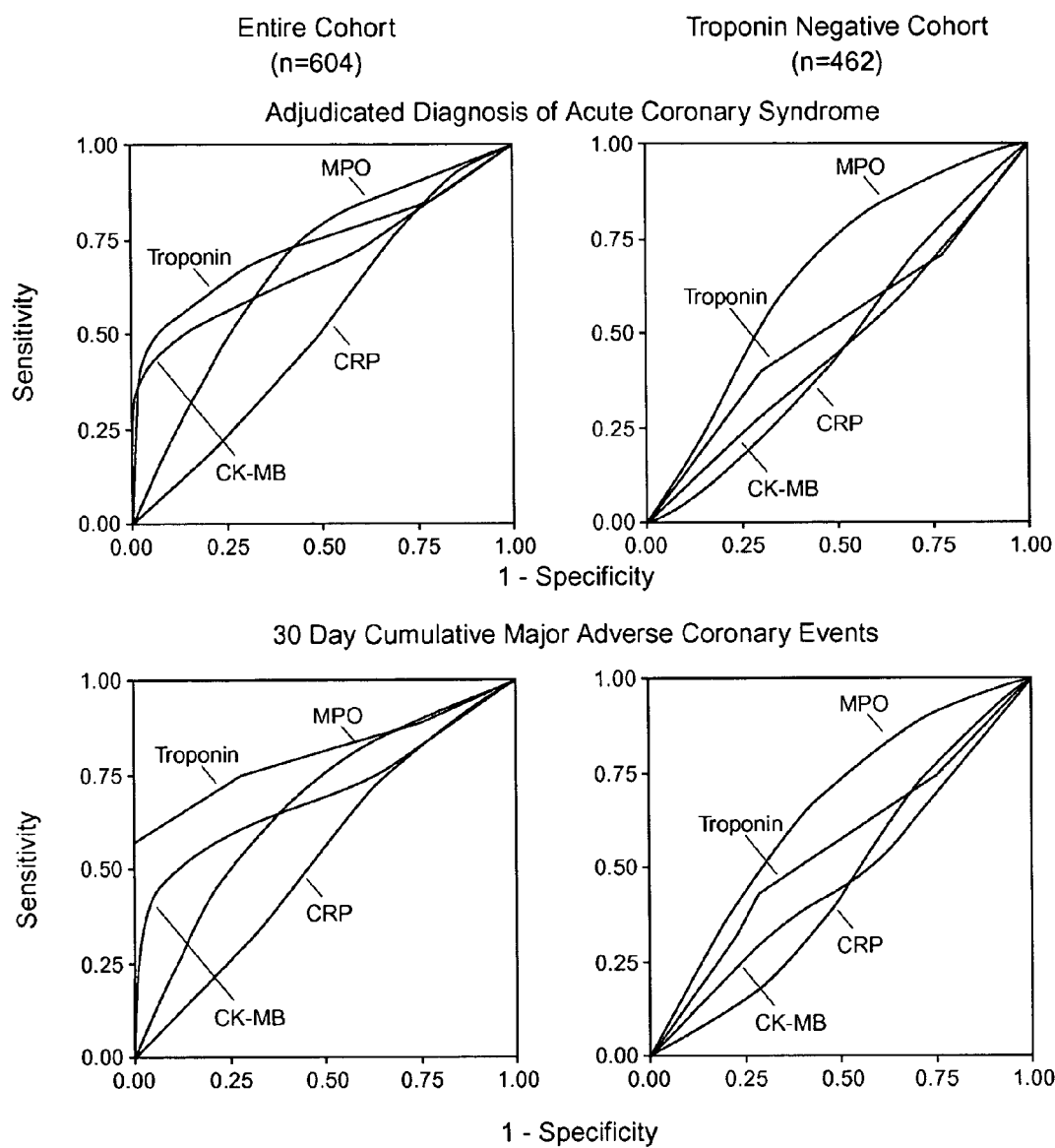
FIG. 2. Receiver Operating Characteristic Curve Analyses of Biochemical Markers for Diagnosis of Acute Coronary Syndrome and 30 day Cumulative Major Adverse Cardiac Events. Shown are receiver operating characteristic curves for Troponin-T (maximum value), creatine kinase-MB (CK-MB, maximum value), C-reactive protein (CRP) and myeloperoxidase (MPO) for all patients (left panel) and for troponin negative patients (right panel).

Receiver operator characteristic curves for prediction of acute coronary syndrome and major adverse cardiac events for the entire cohort, and the troponin negative cohort, were examined (FIG. 2). In troponin negative subjects, areas under the curve were highest for myeloperoxidase compared to troponin (using values <0.01 ng/ml), peak creatine kinase-MB or C-reactive protein (P<0.001 for all comparisons for both outcomes). Using a cutpoint for myeloperoxidase ($\geq$198 pM) derived from the receiver operator characteristic curve for the entire cohort and 30d major adverse cardiac events as the outcome, and established cutpoints for troponin-T, creatine kinase-MB and C-reactive protein,[23] sensitivity, specificity, positive and negative predictive values were calculated for troponin-T (58.0%, 100.0%, 100.0% and 77.7%), creatine kinase-MB (42.4%, 94.7%, 84.6% and 70.7%), C-reactive protein (31.7%, 68.9%, 40.6% and 60.0%) and myeloperoxidase (65.7%, 60.7%, 53.3% and 72.2%).

To evaluate the potential clinical utility of myeloperoxidase, comparisons of predicted positive versus negative test results for troponin-T, creatine kinase MB, C-reactive protein and myeloperoxidase were calculated (Table 3). Myeloperoxidase levels significantly enhanced identification of patients at risk despite negative troponin-T levels at evaluation as compared to other markers (Table 3). The combination of either an elevated troponin-T or an elevated myeloperoxidase significantly improved the ability to identify subjects at risk for 30 day major adverse cardiac events from 58.0% (troponin only) to 84.5% (troponin plus MPO; P<0.001). Among patients classified as having a negative troponin-T, 22.3% went on to experience a major adverse cardiac event in the ensuing 30d period; however, using myeloperoxidase as an additive screening test reduces that number to 14.8%, a 38% reduction (P<0.01 for comparison).

DISCUSSION

The results of the present study reveal that plasma myeloperoxidase levels predict cardiovascular risks independent of C-reactive protein and other markers of inflammation. An initial plasma myeloperoxidase level in patients presenting to the Emergency Department with chest pain provided information useful in determining risks for myocardial infarction at presentation, need for revascularization, and major adverse cardiac events over the next 6 months. Perhaps more importantly, even in patients who "ruled-out" for a myocardial infarction by serial troponins, an elevated baseline plasma myeloperoxidase level was predictive of subsequent major adverse cardiovascular outcomes.

Plasma myeloperoxidase levels correlated with troponin-T levels and were predictive of acute myocardial infarction. However, whereas troponin-T takes 3 to 6 hours following myocardial injury to rise to measurable circulating levels, myeloperoxidase levels were significantly elevated at baseline in patients that presented (even within 2 h onset of symptoms) with negative cardiac enzymes but that later became positive. These findings suggest that myeloperoxidase levels may have utility in the triage of patients in the Emergency Department, and that plasma myeloperoxidase levels may be a marker of unstable angina preceding myocardial necrosis, and therefore a predictor of vulnerable plaque.

Patients that present with chest pain but without evidence of myocardial necrosis are a diagnostically challenging group for risk stratification, and one in which markers of vulnerable plaques are needed. Perhaps the most remarkable finding in the present study are that plasma levels of myeloperoxidase serve as an excellent predictor of risk even in patients who remained troponin-T negative throughout the index presentation. In contrast, C-reactive protein was not significantly predictive in this group. C-reactive protein is reported to serve as a predictor of short-term risk for major adverse cardiac events in a subset of troponin negative subjects with acute coronary syndromes—those with chest pain at rest.[24] However, a significant proportion of troponin negative patients at presentation have more diagnostically challenging histories, and elevated levels of C-reactive protein are seen in less than 50% of patients with myocardial infarction not preceded by unstable angina.[25]

The present studies suggest that myeloperoxidase serves as a marker of the vulnerable plaque. A unique feature of myeloperoxidase is the ability to identify patients at near-term risk for major adverse cardiac events independent of recent myocardial necrosis. The present studies demonstrate that addition of myeloperoxidase to initial risk stratification screens in patients presenting with chest pain can increase the health care provider's ability to identify individuals at increased risk who otherwise might not be identified without invasive diagnostic testing.

REFERENCES

1. Libby P, Ridker P M, Maseri A. Inflammation and Atherosclerosis. Circulation 2002; 105:1135-1143.
2. Cannon C P, Weintraub W S, Demopoulos L A, et al. Comparison of early invasive and conservative strategies in patients with unstable coronary syndromes treated with the glycoprotein IIb/IIIa inhibitor tirofiban. N Engl J Med 2001; 344:1879-1887.
3. Schwartz G G, Olsson A G, Ezekowitz M D, et al. Effects of atorvastatin on early recurrent ischemic events in acute coronary syndromes. The MIRACL study: a randomized controlled trial. JAMA 2001; 285:1711-1718.
4. Antman E M, Tanasijevic M J, Thompson B, et al. Cardiac-specific troponin I levels to predict the risk of mortality in patients with acute coronary syndromes. N Engl J Med 1996; 335:1342-1349.
5. Sabatine M S, Morrow D A, de Lemos J A, et al. Multimarker Approach to Risk Stratification in Non-ST Elevation Acute Coronary Syndromes: Simultaneous Assessment of Troponin I, C-Reactive Protein, and B-Type natriuretic Peptide. Circulation 2002; 105:1760-1763.
6. De Servi S, Mazzone A, Ricevuti G, et al. Expression of neutrophil and monocyte CD11B/CD18 adhesion molecules at different sites of the coronary tree in unstable angina pectoris. Am J Cardiol 1996; 78:564-568.
7. Dinerman J L, Mehta J L, Saldeen T G P, et al. Increased neutrophil elastase release in unstable angina pectoris and acute myocardial infarction. J Am Coll Cariol 1990; 15:1559-1563.
8. Buffon A, Biasucci L M, Liuzzo G, et al. Widespread coronary inflammation in unstable angina. N Engl J Med 2002; 347:5-12.
9. Davis M J, Thomas A. Thrombosis and acute coronary-artery lesions in sudden cardiac ischemic death. N Engl J Med 1984; 310:1137-1140.
10. Naruko T, Ueda M, Haze K, et al. Neutrophil infiltration of culprit lesions in acute coronary syndromes. Circulation 2002; 106-2894-2900.
11. Zhang R, Brennan M L, Fu X, et al. Association between myeloperoxidase levels and risk of coronary artery disease. JAMA 2001; 286:2136-2142.
12. Sugiyama S, Okada Y, Sukhova G K, et al. Macrophage myeloperoxidase regulation by macrophage colony-stimulating factor in human atherosclerosis and implications in acute coronary syndromes. Am J Path 2001; 158:879-891.
13. Klebanoff S J, Waltersdorph A M, Rosen H. Antimicrobial activity of myeloperoxidase. Methods Enzymol 1984; 105: 399-403.
14. Podrez E A, Schmidt D, Hoff H F, Hazen S L. Myeloperoxidase-generated reactive nitrogen species convert LDL into an atherogenic form in vitro. J Clin Invest 1999; 103: 1547-1560.
15. Podrez E A, Poliakov E, Shen Z, et al. A novel family of atherogenic oxidized phospholipids promotes macrophage foam cell formation via the scavenger receptor CD36 and is enriched in atherosclerotic lesions. J Biol Chem 2002; 41:38517-38523.
16. Shabani F, McNeil J, Tippett L. The oxidative inactivation of tissue inhibitor of metalloproteinase-1 (TIMP-1) by hypochlorous acid (HOCl) is suppressed by anti-rheumatic drugs. Free Radic Res 1998; 28:115-123.
17. Fu X, Kassim S Y, Parks W C, Heinecke J W. Hypochlorous acid oxygenates the cysteine switch domain of pro-matrilysin (MMP-7). A mechanism for matrix metalloproteinase activation and atherosclerotic plaque rupture by myeloperoxidase. J Biol Chem 2001; 276:41279-41287.
18. Schmitt D, Shen Z, Zhang R, et al. Leukocytes utilize myeloperoxidase-generated nitrating intermediates as physiological catalysts for the generation of biologically active oxidized lipids and sterols in serum. Biochemistry 1999; 38:16904-16915.
19. Abu-Soud H M, Hazen S L. Nitric oxide is a physiological substrate for mammalian peroxidases. J Biol Chem 2000; 275:37524-37532.
20. Eiserich J P, Baldus S, Brennan M L, et al. Myeloperoxidase, a leukocyte-derived vascular NO oxidase. Science 2002; 296:2391-94.
21. McErlean E S, Deluca S A, van Lente F, et al. Comparison of troponin-T versus creatine kinase-MB in suspected acute coronary syndromes. Am J Cardiol 2000; 85:421-426.
22. Agner, K. 1972. Structure and function of oxidation-reduction enzyme. In: Structure and function of oxidation-reduction enzymes. A. Akeson and A. Ehrenberg, editors. Pergamon Press Inc. Tarrytown, N.Y. 329-335.

23. Pearson T A, Mensah G A, Alexander R W, et al. Markers of inflammation and cardiovascular disease: Application to clinical and public health practice; A statement for healthcare professionals from the Centers for Disease Control and Prevention and the American Heart Association. Circulation 2003; 107:499-511.

24. Liuzzo G, Biasucci L M, Gallimore J R, et al. The prognostic value of C-reactive protein and serum amyloid a protein in severe unstable angina. N Engl J. Med. 1994; 331:417-424.

25. Biasucci L M, Liuzzo G, Colizzi C, et al. Clinical use of C-reactive protein for the prognostic stratification of patients with ischemic heart disease. Ital Heart J 2001; 2:164-171.

TABLE 1

Patient Characteristics

| Clinical Characteristics | Myocardial Infarction at Evaluation | |
|---|---|---|
| | No (n = 462) | Yes (n = 142) |
| Age, yr; mean ± SD | 61.4 ± 13.8 | 66.5 ± 12.8[a] |
| Male gender-no. (%) | 254 (55.0) | 100 (70.4)[a] |
| CAD history-no. (%) | 210 (48.3) | 71 (51.8) |
| Revascularization-no. (%) | 151 (34.4) | 51 (37.2) |
| Diabetes-no. (%) | 108 (24.1) | 52 (36.9)[b] |
| Hypertension-no. (%) | 287 (64.1) | 100 (70.9) |
| Hyperlipidemia-no. (%) | 215 (48.2) | 83 (59.3)[b] |
| Current smoking-no. (%) | 92 (21.9) | 42 (30.9)[b] |
| Smoking history-no. (%) | 259 (59.0) | 92 (67.2) |

[a] $p \leq 0.001$ for comparison with troponin negative subjects
[b] $p < 0.05$ for comparison with troponin negative subjects

TABLE 2

Odds Ratio Associated with Major Adverse Cardiac Events Per Myeloperoxidase and C-Reactive Protein Quartiles

| | Myeloperoxidase Quartile | | | | C-Reactive Protein Quartile | | | |
|---|---|---|---|---|---|---|---|---|
| | 1 | 2 | 3 | 4 | 1 | 2 | 3 | 4 |
| MPO (pM) | <119.4 | 119.4-197.9 | 198.0-393.9 | >394.0 | <1.925 | 1.926-5.470 | 5.471-11.640 | >11.640 |
| Index Presentation | | | | | | | | |
| Myocardial Infarction | 1.0 | 1.2 (0.7-2.3) | 2.1 (1.2-3.8)* | 3.9 (2.2-6.8)**† | 1.0 | 1.9 (1.0-3.6)* | 3.1 (1.7-5.8)** | 3.0 (1.6-5.4)*† |
| All patients TnT negative initially | 1.0 | 1.0 (0.4-2.7) | 1.5 (0.6-3.9) | 3.7 (1.6-8.5)**† | 1.0 | 1.6 (0.7-3.6) | 1.7 (0.8-3.9) | 1.1 (0.5-2.7) |
| Adjudicated ACS | | | | | | | | |
| All patients | 1.0 | 1.6 (1.0-2.7) | 3.5 (2.1-5.8)* | 4.8 (2.9-7.8)* | 1.0 | 1.7 (1.1-2.8)* | 2.0 (1.2-3.2)* | 1.5 (0.9-2.3) |
| TnT negative patients | 1.0 | 2.0 (1.0-4.2) | 4.6 (2.3-9.2)* | 4.1 (2.0-8.5)* | 1.0 | 1.5 (0.8-2.6) | 1.2 (0.6-2.1) | 0.6 (0.3-1.3) |
| MACE, 30 days | | | | | | | | |
| All patients | 1.0 | 1.7 (1.02-2.8)* | 3.2 (2.0-5.4)** | 4.7 (2.8-7.7)**† | 1.0 | 1.9 (1.2-3.1)* | 1.7 (1.0-2.7)* | 1.6 (1.0-2.5) |
| TnT negative patients | 1.0 | 2.2 (1.1-4.6)* | 4.2 (2.1-8.4)** | 4.1 (2.0-8.4)**† | 1.0 | 1.7 (1.0-3.0) | 0.8 (0.4-1.6) | 0.8 (0.4-1.5) |
| MACE, 6 months | | | | | | | | |
| All patients | 1.0 | 1.6 (1.0-2.7) | 3.6 (2.2-5.8)** | 4.7 (2.9-7.7)**† | 1.0 | 1.8 (1.1-2.9)** | 1.7 (1.1-2.7)* | 1.8 (1.1-2.8)*† |
| TnT negative patients | 1.0 | 1.9 (1.0-3.8) | 4.4 (2.3-8.4)** | 3.9 (2.0-7.7)**† | 1.0 | 1.6 (0.9-2.7) | 0.9 (0.5-1.7) | 1.0 (0.6-1.9) |

*$p < 0.05$ relative to first quartile;
**$p < 0.01$ relative to first quartile;
†$p < 0.001$ for trend;
††$p < 0.05$ for trend

TABLE 3

Predicted Positive versus Negative Test Results for Troponin-T. Creatine Kinase-MB, C-reactive Protein and Myeloperoxidase

| Variable | Unstable Angina | | Myocardial Infarction | | Acute Coronary Syndromes | | MACE 30d (All patients) | | MACE 30d (Troponin negative) | |
|---|---|---|---|---|---|---|---|---|---|---|
| | Ratio | $\chi^2$ | Ratio | $\chi^2$ | Ratio | $\chi^2$ | Ratio | $\chi^2$ | Ratio | $\chi^2$ |
| Troponin-T | 0:103 | 38.0** | 142:0 | 604.4** | 142:103 | 270.2** | 142:103 | 271.4** | 0:0 | — |
| Creatine Kinase-MB | 5:98 | 18.0** | 98:44 | 273.0** | 103:142 | 120.3** | 104:141 | 121.1** | 6:97 | 0.03 |
| C-Reactive Protein | 24:79 | 3.5 | 55:82 | 5.6* | 79:161 | 0.3 | 76:164 | 0.007 | 21:82 | 4.3* |
| Myeloperoxidase | 67:36 | 11.5** | 96:46 | 22.2** | 163:82 | 45.0** | 161:84 | 39.7** | 65:38 | 18.1** |

Additive Value of Markers plus Troponin-T for Prediction of Positive Test Results

| | MACE 30d (All patients) | | Cut points for variables used were as follows: Troponin-T |
|---|---|---|---|
| Variable | Variable alone N (%) | Variable Plus Troponin T N (%) | ($\geq$0.1 ng/ml). creatine kinase-MB ($\geq$8.8 ng/ml). C-reactive protein ($\geq$10 mg/L) and myeloperoxidase ($\geq$198 pM). |
| Troponin-T | 142 (58.0) | — | Note that myeloperoxidase predicts risk for major adverse cardiac events (MACE) in the ensuing 30 days |
| Creatine Kinase MB | 104 (42.5) | 148 (60.4) | following presentation to the Emergency Department in troponin negative subjects. Addition of myeloperoxidase |
| C-Reactive Protein | 76 (31.7) | 163 (66.5) | to Troponin-T as a risk stratification strategy also significantly increases the sensitivity for prediction of |
| Myeloperoxidase | 161 (65.7) | 207 (84.5) | major adverse cardiac events. *p < 0.05. **p < 0.001 |

What is claimed is:

1. A method of determining if a patient presenting with chest pain is at risk of experiencing a major adverse cardiac event within the subsequent 6 months, comprising:

comparing levels of myeloperoxidase (MPO) activity, myeloperoxidase (MPO) mass, or both, in a bodily sample from a patient with chest pain to at least one control value that is based on the levels of MPO activity, MPO mass, or both in a comparable bodily sample from a control population, wherein the bodily sample is blood, plasma, serum or circulating leukocytes, and wherein a patient whose bodily sample contains elevated levels of MPO activity, MPO mass, or both as compared to the at least one control value is at risk of experiencing a major cardiac event within 6 months of presenting with chest pain.

2. The method of claim 1, wherein cellular distribution of myelopcroxidase levels in the patient's bodily sample is obtained by flow cytometry.

3. The method of claim 1, wherein said at least one control value is based on the MPO activity levels in comparable bodily samples from the general population or a select population of human subjects.

4. The method of claim 1, wherein said at least one control value is a single representative value or a range of representative values and is based on the MPO activity levels in comparable bodily samples from the general population or a select population of human subjects.

5. The method of claim 1, wherein the patient's MPO activity level is compared to a plurality of MPO activity level ranges that are based on the MPO activity levels in comparable bodily samples from the general population or a select population of human subjects.

6. The method of claim 1, wherein the circulating leukocytes are one or more of the following: neutrophils, monocytes, sub-populations of neutrophils, and sub-populations of monocytes.

7. The method of claim 1, wherein the levels of myeloperoxidase mass in the human patient's bodily sample is obtained by an immunological technique.

8. The method of claim 1, wherein said control value is based upon the MPO mass levels in comparable bodily samples from the general population or a select population of human subjects.

9. The method of claim 1, wherein said at least one control value is a single representative value or a range of representative values and is based upon the MPO mass levels in comparable bodily samples from the general population or a select population of human subjects.

10. The method of claim 1, wherein the patient's MPO mass level is compared to a plurality of MPO mass level ranges that are based on the MPO mass levels in comparable bodily samples from the general population or a select population of human subjects.

11. The method of claim 1, wherein a patient whose bodily sample contains elevated levels of MPO activity, MPO mass, or both as compared to the at least one control value is at risk of experiencing a major cardiac event within 1 months of presenting with chest pain.

12. The method of claim 1, wherein the sample is blood, serum, plasma, or any combination thereof.

13. The method of claim 12, further comprising the step of determining levels of troponin in the patient's blood, serum, plasma, or any combination thereof.

14. The method of claim 13, wherein levels of troponin in the patient's blood, serum, and/or plasma are normal.

15. The method of claim 13, wherein levels of troponin in the patient's blood, serum, and/or plasma are elevated.

16. A method of determining if a patient with chest pain is at risk of experiencing a major cardiac event within 6 months of presenting with chest pain, comprising:

a) obtaining the levels of one or more select myeloperoxidase-generated oxidation products in a bodily sample from the human patient, wherein said bodily sample is urine, blood, serum, or plasma, wherein each of said select myeloperoxidase-generated oxidation product is selected from the group consisting of nitrotyrosine, dityrosine, methionine sulphoxide and an MPO-generated lipid peroxidation product; and b) comparing the levels of each of said select myeloperoxidase-generated oxidation product in the bodily sample from the human patient with a control value;

wherein a patient whose bodily sample contains elevated levels of said one or more myeloperoxidase-generated oxidation products as compared to the at least one control value is at risk of experiencing a major cardiac event within 6 months of presenting with chest pain.

17. The method of claim 16, wherein one of said select myeloperoxidase-generated oxidation product is nitrotyrosine.

18. The method of claim 16, wherein one of said select myeloperoxidase-generated oxidation product is an MPO lipid peroxidation product selected from hydroxy-eicosatetraenoic acids (HETEs); hydroxy-octadecadienoic acids (HODEs), F2Isoprostanes; the glutaric and nonanedioic monoesters of 2-lysoPC (G-PC and ND-PC, respectively); the 9-hydroxy-10-dodecenedioic acid and 5-hydroxy-8-oxo-6-octenedioic acid esters of 2-lysoPC (HDdiA-PC and HOdiA-PC, respectively); the 9-hydroxy-12-oxo-10-dodecenoic acid and 5-hydroxy-8-oxo-6-octenoic acid esters of 2-lysoPC (HODA-PC and HOOA-PC, respectively); the 9-keto-12-oxo-10-dodecenoic acid and 5-keto-8-oxo-6-octenoic acid esters of 2-lysoPC (KODA-PC and KOOA-PC, respectively); the 9-keto-10-dodecendioic acid and 5-keto-6-octendioic acid esters of 2-lysoPC (KDdiA-PC and KOdiA-PC, respectively); the 5-oxovaleric acid and 9-oxononanoic acid esters of 2-lysoPC (OV-PC and ON-PC, respectively); 5-cholesten-5α, 6α-epoxy-3β-ol (cholesterol α-epoxide); 5-cholesten-5β, 6β-epoxy-3β-ol (cholesterol β-epoxide); 5-cholesten-3β,7β-diol (7-OH-cholesterol); 5-cholesten-3β, 25-diol (25-OH cholesterol); 5-cholesten-3β-ol-7β-hydroperoxide (7-OOH cholesterol); and cholestan-3β, 5α, 6β-triol (triol).

19. The method of claim 16, wherein the level of said myeloperoxidase-generated oxidation product in the patient's bodily sample is compared to a representative value or a range of representative values that are based upon the levels of said select myeloperoxidase oxidation product in comparable bodily samples from the general population or a select population of human subjects.

20. The method of claim 16, wherein the control value is a plurality of ranges that are based on the levels of said select myeloperoxidase oxidation product in comparable bodily samples from the general population or a select population of human subjects.

21. A method of assessing the risk of requiring medical intervention in a patient who is presenting with chest pain, comprising
characterizing the levels of myeloperoxidase activity, myeloperoxidase mass, or both, respectively in the bodily sample from the human patient, wherein said bodily sample is blood or a blood derivative,
wherein a patient whose levels of myeloperoxidase activity, mycloperoxidase mass, or both is characterized as being elevated in comparison to levels of myeloperoxidase activity, myeloperoxidase mass or both in a comparable bodily samples obtained from individuals in a control population is at risk of requiring medical intervention to prevent the occurrence of an adverse cardiac event within the next six months.

22. A method of determining whether a patient who presents with chest pain is at risk of requiring medical intervention to prevent an adverse cardiac event within the next six months comprising:
comparing the level of a risk predictor in a bodily sample from the subject with a value that is based on the level of said risk predictor in comparable samples from a control population, wherein said risk predictor is myeloperoxidase activity, myeloperoxidase mass, a myeloperoxidase-generated oxidation product, or any combination thereof, and wherein said bodily sample is blood, serum, plasma, or urine,
wherein a subject whose bodily sample contains elevated levels of said risk predictor as compared to the control value is at risk of requiring medical intervention to prevent an adverse cardiac event within 6 months of presenting with chest pain, and
wherein the difference between the level of the risk predictor in the patient's bodily sample and the level of the risk predictor in a comparable bodily sample from the control population establishes the extent of the risk to the subject of requiring medical intervention to prevent an adverse cardiac event within the next six months.

23. The method of claim 22, wherein the risk predictor is mycloperoxidase mass or myeloperoxidase activity,
wherein the sample is blood, serum or plasma,
wherein levels of troponin in the patient's blood, serum, or plasma are normal and,
wherein the patient is categorized as being at risk of requiring medical intervention within the next 6 months based on levels of myeloperoxidase activity or myeloperoxidase mass or in the patient's blood, plasma or serum.

24. The method of claim 22, wherein the difference between the level of the risk predictor in the patient's bodily sample and the level of the risk predictor in a comparable bodily sample from the control population establishes the extent of the risk to the patient of requiring medical intervention within the next 30 days.

* * * * *